(12) United States Patent
Millay et al.

(10) Patent No.: US 7,427,268 B2
(45) Date of Patent: Sep. 23, 2008

(54) RING-SHAPED CUFF FOR MEASUREMENT OF BLOOD PRESSURE

(75) Inventors: Jack Millay, Beaverton, OR (US); Paul Patterson, Beaverton, OR (US)

(73) Assignee: Pharma-Smart, LLC, Victor, NY (US)

( * ) Notice: Subject to any disclaimer, the term of this patent is extended or adjusted under 35 U.S.C. 154(b) by 23 days.

(21) Appl. No.: 10/898,782

(22) Filed: Jul. 26, 2004

(65) Prior Publication Data
US 2005/0171445 A1  Aug. 4, 2005

Related U.S. Application Data

(63) Continuation-in-part of application No. 10/771,251, filed on Feb. 3, 2004, now Pat. No. 7,166,077.

(51) Int. Cl.
*A61B 5/02* (2006.01)

(52) U.S. Cl. ..................................................... 600/499

(58) Field of Classification Search .......... 600/481–507
See application file for complete search history.

(56) References Cited

U.S. PATENT DOCUMENTS

| | | | | |
|---|---|---|---|---|
| 2,456,086 A * | 12/1948 | Schwall, Jr. | ................. | 114/345 |
| 2,678,040 A | 5/1954 | Poole et al. | | |
| 2,850,422 A * | 9/1958 | Welch, Jr. | ..................... | 53/410 |
| 3,208,661 A * | 9/1965 | Hewitt et al. | ............... | 383/61.1 |
| 3,355,997 A * | 12/1967 | Heimos et al. | .............. | 493/189 |
| 3,371,849 A * | 3/1968 | Rochla | ......................... | 383/44 |
| 3,467,077 A * | 9/1969 | Cohen | ......................... | 600/499 |
| 3,760,795 A * | 9/1973 | Adelhed | ..................... | 600/499 |
| 3,941,384 A * | 3/1976 | Wopschall | .................. | 273/386 |
| 4,091,732 A * | 5/1978 | Schadow | ..................... | 102/374 |
| 4,160,464 A * | 7/1979 | Ballinger | ..................... | 138/93 |
| 4,331,155 A * | 5/1982 | Sacks | ......................... | 600/499 |
| 4,844,084 A * | 7/1989 | Yamasawa | .................. | 600/494 |
| 4,850,369 A * | 7/1989 | Yamasawa | .................. | 600/499 |
| 5,108,370 A * | 4/1992 | Walinsky | ............... | 604/102.02 |
| 5,193,549 A * | 3/1993 | Bellin et al. | ................. | 600/499 |
| 5,511,551 A * | 4/1996 | Sano et al. | ................... | 600/499 |
| 5,593,454 A * | 1/1997 | Helmy | ......................... | 623/32 |
| 5,746,213 A * | 5/1998 | Marks | ......................... | 600/499 |
| 6,213,953 B1 * | 4/2001 | Reeves | ........................ | 600/499 |
| 6,224,558 B1 * | 5/2001 | Clemmons | .................. | 600/490 |
| 6,290,653 B1 | 9/2001 | Che et al. | | |
| 6,699,199 B2 * | 3/2004 | Asada et al. | ................. | 600/504 |

(Continued)

*Primary Examiner*—Robert L. Nasser, Jr.
*Assistant Examiner*—Karen E Toth
(74) *Attorney, Agent, or Firm*—Robert C. Brown; Neal L. Slifkin

(57) ABSTRACT

A closed blood pressure cuff including a ring-shaped inflatable bladder having an inner portion for making direct contact with a user's arm and an outer portion having a fixed circumference outside the inner portion. The bladder is formed of non-distensible material, preferably by joining a tubular starting element. The inner portion of the bladder is not constrained during inflation and thus can readily conform to a subject's limb, the outer portion accommodating an upper limit of arm circumference within the cuff. The cuff may include a stiffener attached to the outer portion of the bladder to automatically adjust the shape of the bladder during inflation. The stiffener may be in the form of a continuous layer or may comprise a plurality of axial ribs, allowing the cuff to be folded when not in use. The cuff may be generally cylindrical or may be tapered.

17 Claims, 11 Drawing Sheets

U.S. PATENT DOCUMENTS

2004/0040082 A1* 3/2004 Fireman et al. ............... 4/506
2004/0186385 A1* 9/2004 Mochizuki .................. 600/499
2005/0096552 A1* 5/2005 Law et al. ................... 600/485
2007/0135720 A1* 6/2007 Vinocur ...................... 600/499
2007/0203416 A1* 8/2007 Lowe ......................... 600/485

* cited by examiner

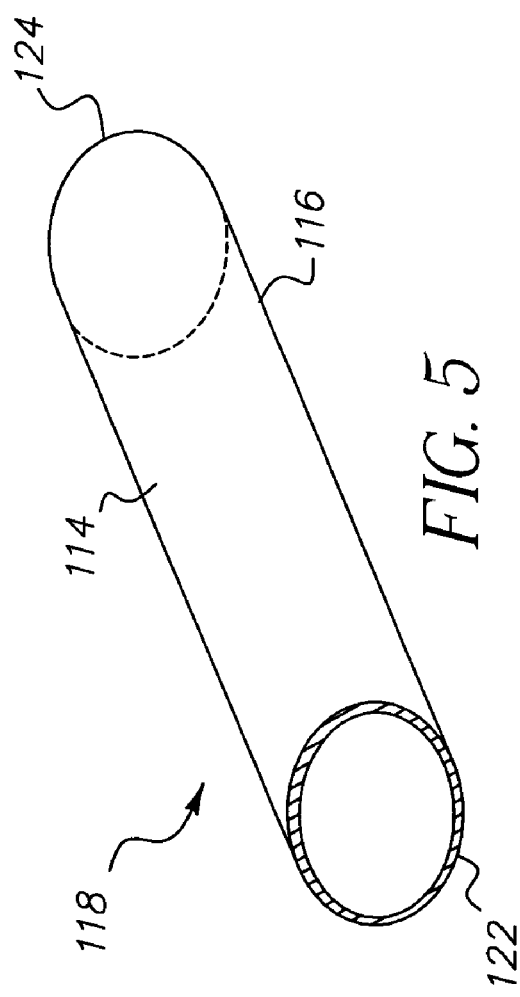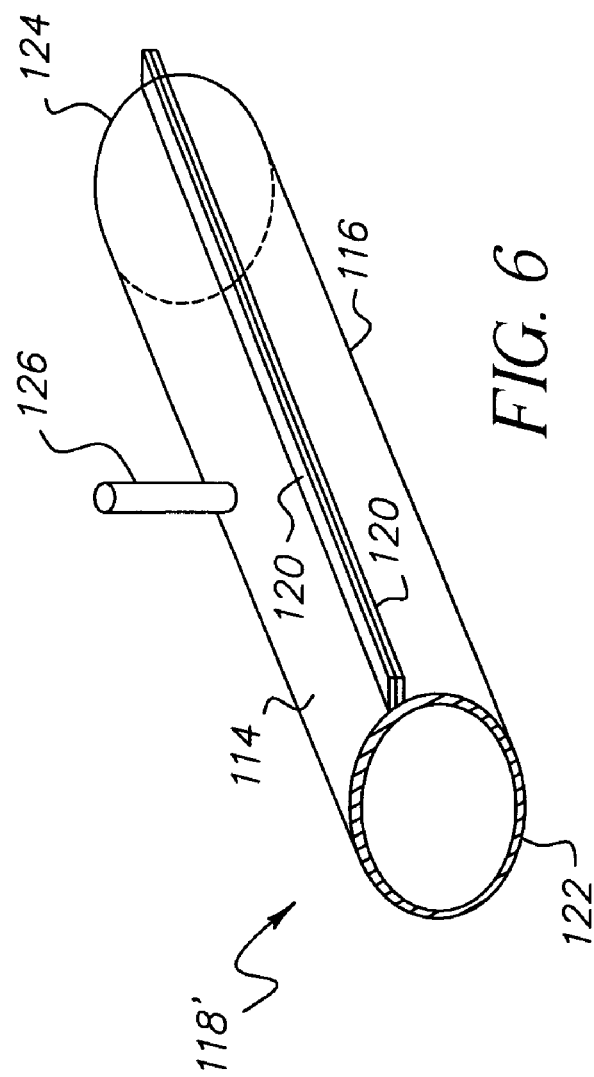

RING-SHAPED CUFF FOR MEASUREMENT OF BLOOD PRESSURE

RELATIONSHIP TO OTHER APPLICATIONS AND PATENTS

The present application is a Continuation-In-Part of a U.S. patent application, Ser. No. 10/771,251, filed Feb. 3, 2004 now U.S. Pat. No. 7,166,077.

TECHNICAL FIELD

The present invention relates to devices for measuring systolic, mean, and diastolic blood pressures in animals; more particularly, to inflatable devices for measuring such blood pressures in humans; and most particularly, to an improved ring-shaped (also referred to herein as "closed" or "cylindrical") inflatable cuff for obtaining more accurate blood pressure measurements over a greater range of arm sizes.

BACKGROUND OF THE INVENTION

The measurement of systolic, mean, and diastolic blood pressures, referred to herein collectively as "blood pressure," is an important and well-known diagnostic procedure in animal medicine, and especially in human medicine. Blood pressure may be measured either directly, by insertion of a pressure-measuring catheter into an artery, or indirectly (inferentially), usually by means of an inflatable cuff. In using a cuff, the operative principle is that pneumatically inflating the cuff compresses an underlying artery in the subject, and the respective pressures are determined as air pressure is gradually released from the cuff.

In design, known cuffs are either open or closed. An open cuff is a flat device which is wrapped and secured to itself around the subject's extremity. A closed cuff is a generally cylindrical inflatable device through which a subject's extremity is inserted and which is not adjustable as to its relaxed circumference.

In operation, a typical cuff is applied to encircle an upper arm, thigh, or in some cases, a wrist or forearm. The cuff is then inflated to an indicated cuff air pressure at which the flow of blood through the underlying artery is stopped, such air pressure being greater than the subject's systolic pressure. Pressure within the cuff is then gradually reduced. When blood flow through the artery resumes, the cuff pressure corresponds to the subject's systolic pressure. When pressure in the cuff drops below the subject's diastolic pressure, blood flows in the artery through the complete cardiac cycle. Optionally, mean blood pressure may also be determined.

The onset of these flow phenomena can be determined in any of several ways: for example, a) by listening via a stethoscope to the sounds emanating from the artery downstream of the cuff; b) by observing the relatively small changes in pressure in the cuff caused by the encircled artery's opening and closing during the cardiac cycle; or, c) by using a Doppler flowmeter to measure flow rates. Each of these methods is well known in the art.

There are several potential sources of error in determining blood pressure using a prior art inflatable open cuff. An important consideration is that the dimensions of the cuff be selected to fit the subject to be tested. The contact dimension of a cuff in a direction along a subject's arm is referred to herein as the cuff contact width, and the contact dimension circumferential of the relaxed arm is the circumference, or contact length. Preferably, the contact width of the cuff is about 40% of the arm circumference, and the contact length of the inflatable part of the cuff is at least 70% of the arm circumference. If the total contact width of the cuff is too narrow, blood pressure is over-estimated; if the width is too large, blood pressure is under-estimated. The contact area, contact width times contact length, also is important as is well known in the art.

There are three types of blood pressure determining devices: a) automated "public use" devices that have a single fixed-size cuff; b) automated devices that typically allow for a selection of cuffs by an operator; and c) manual devices that also typically allow for a selection of cuffs. As used herein, the term "public use" refers to a simple to use, complete blood pressure measuring device that is intended to be used without assistance on a number of people that are likely to have varying arm sizes.

In common medical practice using selectable cuffs, a wrap-around (flat) cuff is normally used. An assortment of cuff sizes is required to cover the full range of arm sizes to be accommodated. In stand-alone uses today (stand-alone being defined as not being part of an automated public use blood pressure machine), a "wrap-around" cuff is typically employed. Such a cuff comprises an elongate flat fabric pocket formed of non-elastic material into which a distensible bladder is inserted for pneumatic inflation. An alternative form of cuff comprises a non-distensible bladder formed integrally with the cuff wrap. In either case, the cuff is wrapped snugly around the subject's extremity, such as an arm or leg, and is then secured in place, for example, by hook and loop attachments. (As used hereinbelow, the term "arm" should be taken generally to mean any of the various anatomical extremities or appendages in which blood pressure may be measured with a cuff.)

Because proper bladder contact sizing is important for accurate blood pressure measurement, the circumference of a subject's arm should be determined before attempting blood pressure measurement in order to select the proper cuff size. In good medical practice, the circumference of the subject's arm determines the size cuff to be used. For adult humans, a choice of cuffs may include three sizes standard in the art: Small Adult, Normal Adult, and Large Adult. Each cuff is sized for an arm circumference in the middle of a range which overlaps the range of an adjacent cuff. For example, a Normal Adult cuff may be specified for use on arm circumferences of 25-35 cm, and a Large Adult cuff may be specified for circumferences of 33-47 cm. Either cuff may be used on a 34 cm arm, but neither cuff is optimal because the contact width of the cuff is optimized for the middle of each range. Blood pressure measurements of a given subject using the two different cuffs may differ by several mmHg. Of course, a greater number of different cuffs, each having a narrower range of arm sizes, would lessen this error but would require a large and unwieldy inventory of open cuffs at each measurement site.

Unfortunately, it is common in stand-alone use to ignore the benefits of sizing the cuff to the subject and to simply use one cuff for all subjects, with concomitant sacrifices in accuracy. This error is frequently compounded by improper application. What is needed in the stand-alone art is a single closed cuff that can provide accurate blood pressure measurement over a very wide range of arm sizes with a minimum of care or expertise by the user.

Prior art closed cuffs also present a serious problem in use. As noted above, a well-known prior art use for closed cuffs is as a component in automated public use measurement machines. Such machines are intended to make correct measurements on the majority of the population of human users using a single cuff. Because the cuff is closed, the nominal outer and deflated inner diameters are fixed at manufacture to accommodate the largest arm intended for measurement, and the inflation means is attached to the fabric of the pocket. Therefore, the cuff must expand radially inwards first to occupy the slack space necessary to permit insertion of an arm into the cuff, and then further to properly compress the inserted arm.

The main source of error in using an oversize prior art closed cuff arises from severe puckering of the cuff material. Equipment recommendations promulgated by the American Heart Association and the American Association of Medical Instrumentation require that a cuff encircle (make contact with) at least 70% of an arm. In the prior art, an inflation chamber is formed by heat sealing and then stitching or gluing together two air-impermeable layers of non-distensible, non-elastic material along all four edges thereof to form a pillow-shaped bladder. An outer material shell and seam tape are also stitched into the cuff, making the cuff relatively stiff and non-compliant. As the bladder is inflated, the inner layer is forced into relatively large radial puckers or wrinkles, and especially so if the subject's arm is relatively small in circumference. These puckers constitute breaks in the encircling pressure and can reduce the encircling contact area to less than the recommended 70%. Such puckers can lead to outright failure of the measurement when a pucker is formed over the brachial artery being tested.

Further, bladder pressure significantly higher than systolic may be required to close the puckers and the underlying artery, thus giving a falsely high measurement of systolic pressure. Further, because the bladder layers are constrained along all four edges, the bladder cannot readily collapse transversely to form a desirable oval cross-sectional shape. In order to overcome the bladder constraints, additional internal pressure is required to inflate the bladder into contact the subject's arm. Once arm contact has been made, this added pressure is not transferred to the arm, thus producing a sizeable error, particularly with smaller arms.

What is needed is an improved blood pressure closed cuff that can provide accurate measurement in an automated blood pressure machine over the range of arm sizes of potential human users. In addition, there is a need for a closed cuff for stand-alone use that eliminates cuff selection and application errors.

It is a principal object of the present invention to make accurate measurements of blood pressure over a wide range of human arm sizes using a single closed cuff.

It is a further object of the invention to make such measurements via an automated public use blood pressure machine.

It is a still further object of the invention to make such measurements in stand-alone use.

SUMMARY OF THE INVENTION

Briefly described, a closed blood pressure cuff in accordance with the invention includes a ring-shaped inflatable bladder having an inner portion for making direct contact with a user's arm and an outer portion having a fixed and predetermined circumference outside the inner portion. In simplest embodiment, the cuff comprises only the bladder. The bladder is formed of a highly flexible but resiliently non-distensible material and has at least one entrance port or nipple for inflation and deflation. The bladder preferably is formed from a tubular starting element joined toroidally like a deflated tire inner tube. Preferably, the bladder includes a transverse seam which may be formed either by sealing together the opposite ends of the tubular starting element or by creating a pseudo seam by sealing together the inner and outer portions at some other location. The inner portion of the bladder is not constrained during inflation and thus can readily conform to a subject's limb, the outer portion having a fixed outer circumference selected to accommodate an upper limit of arm circumference within the cuff. The width of this cuff is chosen to be appropriate for the largest diameter arm that can be inserted into the cuff. When a smaller arm is inserted, the cuff automatically narrows during inflation, making the width appropriate for a smaller size arm, thus making the cuff useful over a much wider range of arm sizes than can be accommodated by any single prior art cuff.

The cuff may include a stiffener attached to the outer portion of the bladder. By axially constraining the outer portion during inflation, the stiffener automatically adjusts the cross-sectional shape of the bladder during inflation to provide a wide contact surface for larger circumference arms and increasingly narrower contact surfaces for smaller circumference arms, even more than the cuff without the stiffener. This provides the means to extend the range of arm sizes even further than the cuff without the stiffener. A stiffener also provides the means to follow the 40% width recommendation much more closely over any given range of arm sizes.

The stiffener may be attached to the outside of the outer portion or may be attached within the bladder, to equal effect. The stiffener may be in the form of a continuous layer or may comprise a plurality of axial ribs, allowing the cuff to be folded when not in use. Preferably, the stiffener extends over less than the full width of the cuff, to extend the range of the cuff for small arms.

The cuff may be generally cylindrical or may be frusto-conically tapered.

A cuff in accordance with the invention is well suited for use in either an automated blood pressure measurement machine or stand-alone measurement.

BRIEF DESCRIPTION OF THE DRAWINGS

The present invention will now be described, by way of example, with reference to the accompanying drawings, in which:

FIG. 5 is an isometric view showing a length of seamless tubing suitable for forming the improved closed cuff embodiment shown in FIG. 4;

FIG. 6 is an isometric view showing a length of seamed tubing suitable for forming an improved closed cuff in accordance with the invention, the tubing having an inflation/deflation nipple;

DESCRIPTION OF THE PREFERRED EMBODIMENTS

Figure 1:
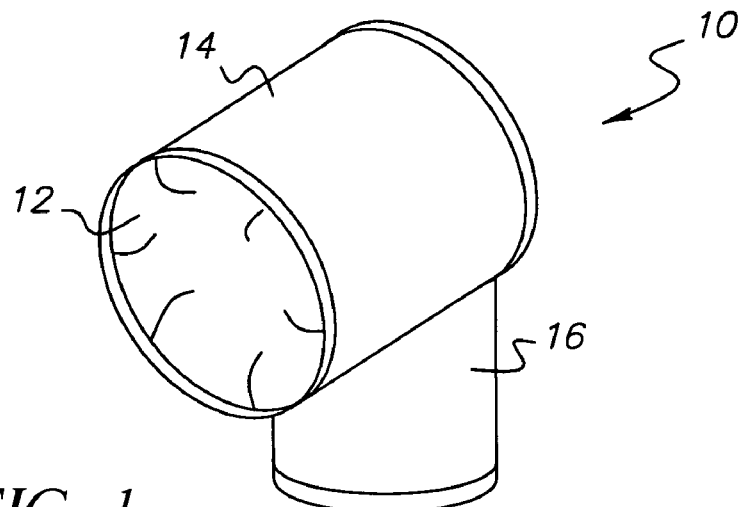
FIG. 1 is an isometric view of a prior art closed cuff in an automated blood pressure measurement machine.
Figure 2:
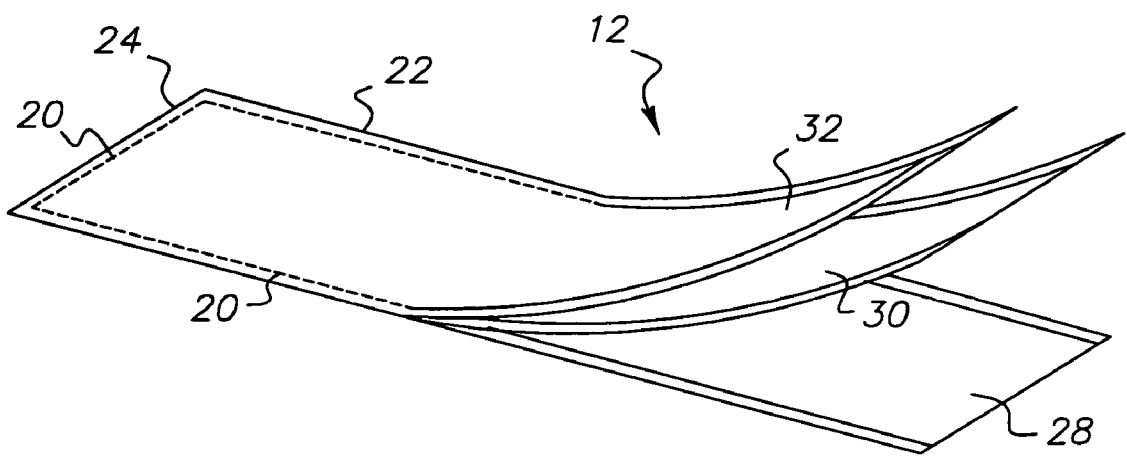
FIG. 2 is an isometric view showing the arrangement of layers in a prior art cuff.
Figure 3:
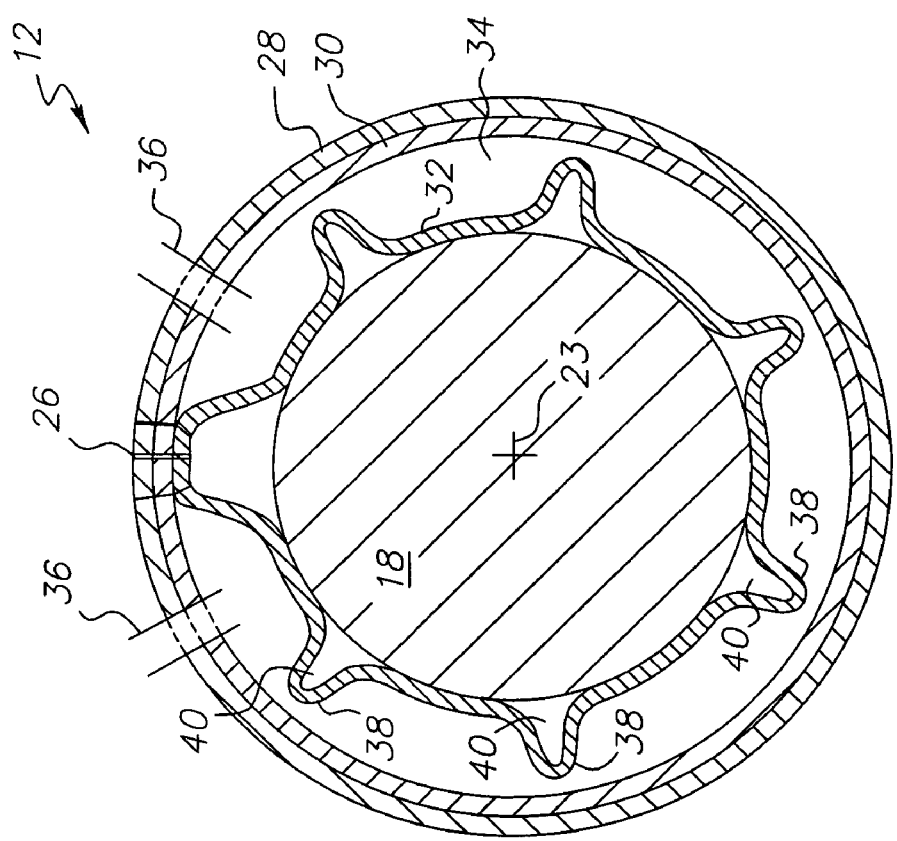
FIG. 3 is a cross-sectional view of an inflated prior art closed cuff, taken transverse to an axis thereof.
Figure 7:
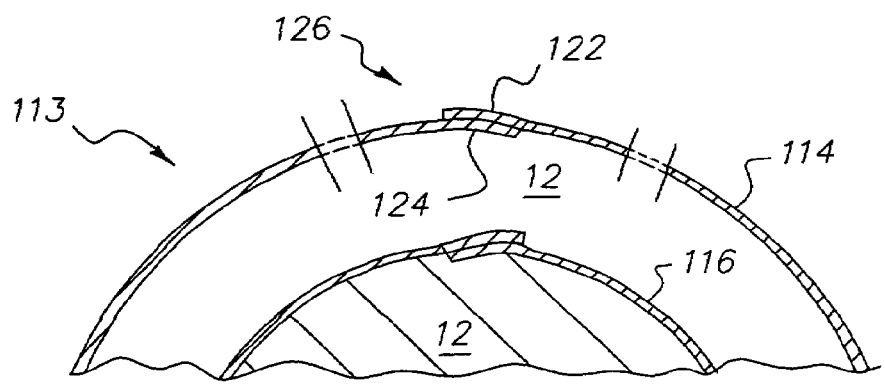
FIGS. 7 through 9 are transverse cross-sectional views showing three exemplary alternative means for sealing the tubings shown in FIGS. 5 and 6 into closed cuffs in accordance with the invention.
Figure 8:
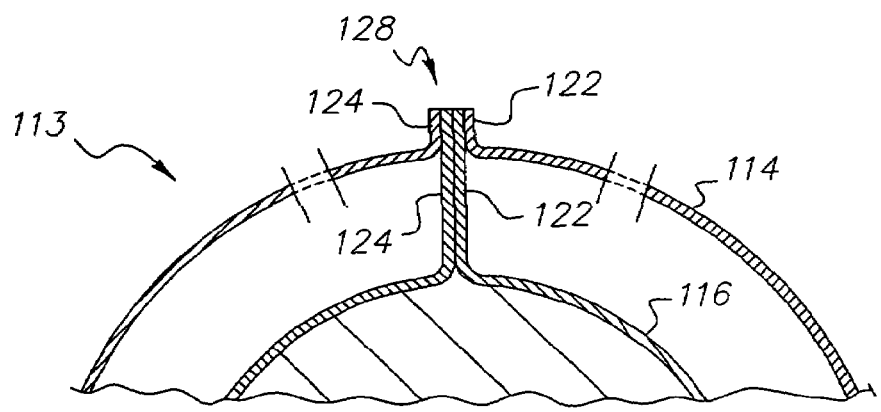

Referring to FIGS. 1 through 3, a user-interface portion of an automated blood pressure measurement machine 10 includes a generally cylindrical closed inflatable cuff 12 disposed within a rigid cylindrical housing 14 being supported by a brace 16. Cuff 12 is connected pneumatically to an actuation and control portion (not shown) of the machine whereby pressurized air is supplied to and withdrawn from the cuff in known fashion. When inflated, cuff 12 selectively compresses an artery in a user's arm 18, after the arm has been inserted through the cuff to position the cuff around the user's bicep, to determine inferentially the blood pressures of the cuff user. Cuff 12 may be a prior art closed cuff 12 (FIG. 3) or an improved closed cuff as described hereinbelow.

A typical prior art closed cuff 12 is formed from at least three layers of flat fabric cut from fabric material stock and joined as by stitching 20 and sealing along the longitudinal 22 and transverse 24 edges. The stitched sub-assembly is then rolled around an axis 23 into a closed form approximating a cylinder and the ends are joined 26 as by gluing or stitching. The outer fabric layer 28 is formed typically of a heavy gauge, long-wearing, non-distensible material such as woven nylon shell. The intermediate and inner fabric layers 30,32 are formed also of non-distensible material such as nylon shell but are additionally treated to make them substantially leak-proof against air, the space therebetween defining a pneumatic pressure chamber 34. Chamber 34 is connectable to the actuation and control portion of the machine (not shown) via one or more air nipples 36 extending through layers 28,30. Because layers 30,32 are formed and joined together as planar elements, as shown in FIG. 2, they exhibit severe transverse puckers 38 when the planar sub-assembly is rolled into a closed cuff, which puckers are exacerbated in at least inner layer 32 after inflation of the cuff, as shown in FIG. 3. Puckers 38 define voids 40 which represent areas of non-contact of cuff 12 with the subject's arm 18. As already noted, such areas can seriously compromise the accuracy of blood pressure measurement. It is an important feature of an improved cuff in accordance with the invention to minimize the size of such puckers, through novel configuration of the cuff and selection of materials.

Referring to FIGS. 4 through 9, a first embodiment 112 of an improved inflatable closed cuff in accordance with the invention includes a ring-shaped bladder 113, also referred to herein as a "toroidal" bladder. Bladder 113 includes an outer portion 114 and an inner portion 116 and may be formed from seamless tubing stock 118, as is shown in FIG. 5. Alternatively, a seamed tubing stock 118' may be formed from a flat piece of stock by folding over and joining longitudinal edges 120 as by stitching, gluing, or heat sealing, for example, as shown in FIG. 6. The seam may be a projection seam having the same side of the material joined to itself, as shown in FIG. 6, or an overlap seam (not shown) having opposite sides of the material joined to each other. It is not desirable to form the tubing stock as in the prior art by stitching together two pieces of flat stock along all four mutual edges.

Prior to being rolled into bladder 113, open tubing stock 118,118' includes first and second ends 122,124 and inner and outer portions 114,116. An inflation nipple 126 may be included in the seam of tubing stock 118' or may be disposed otherwise through the tubing as shown in FIG. 6.

Tubing 118,118' is preferably formed of a thin, highly flexible but non-distensible, polymeric sheeting which is air-impervious, for example, polyurethane-coated nylon mesh coated on both sides. Such material is highly compliant and thus puckers 119, which must form against a user's arm 18 to accommodate the smaller diameter of the inner portion 114, are compressed 119a and/or flattened 119b and therefore do not cause significant voids in the cuff circumferential contact. This material has the added advantage that it is readily sealed to itself by conventional heat-sealing, which is useful in forming the bladder.

Figure 4:
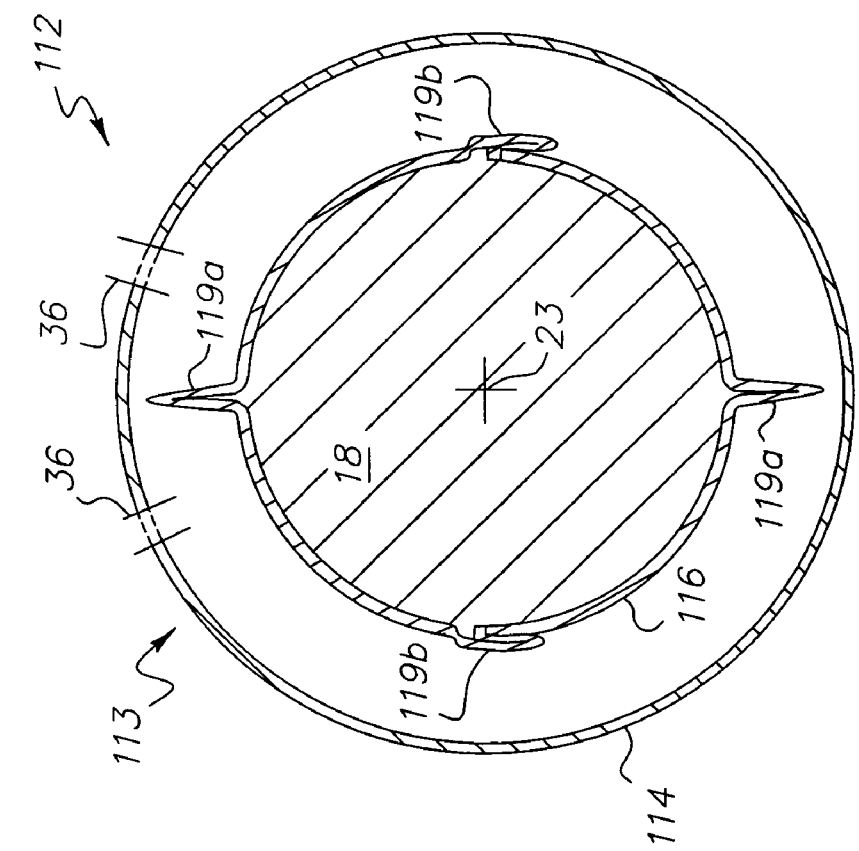
FIG. 4 is a transverse cross-sectional view of a first embodiment of an improved closed cuff in accordance with the invention.
Figure 9:
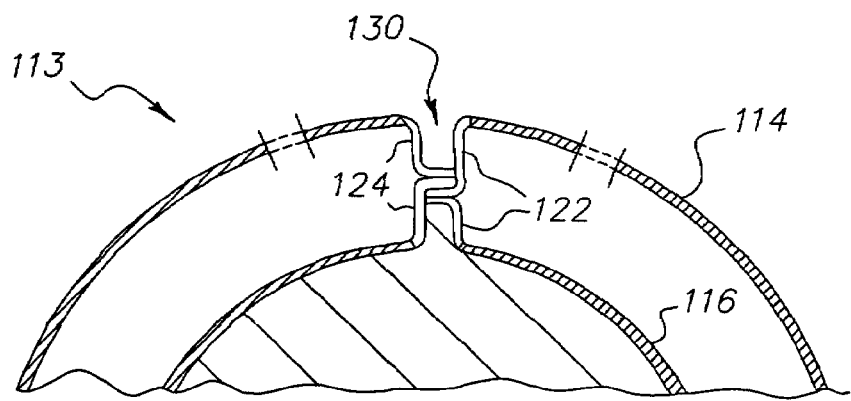

Bladder 113 may be formed as a continuous ring-shaped element similar to an inner tube for an automotive tire, as shown in FIG. 4. Alternatively, bladder 113 may be formed by connecting together ends 122,124 in any of several ways, some of which are shown exemplarily in FIGS. 7 through 9. A telescopic lap seal 126 may be formed by inserting end 124 into end 122 (FIG. 7); or, a first type of transverse seal 128 may be formed by sealing ends 122,124 of inner portion 116 between ends 122,124 of outer portion 114 (FIG. 8); or, a second type of transverse seal 130 may be formed by interleavingly sealing ends 122,124 of inner portion 116 with ends 122,124 of outer portion 114 (FIG. 9). A transverse seal such as seal 128,130 is presently preferred because it defines an axially-oriented seam in bladder 113 that acts to prevent the doughnut-shaped bladder from rolling off a user's arm when bladder 113 is inflated. When a telescopic seam such as seam 126 is used, it may be preferable to provide an additional axially-sealed area ("pseudo seam") formed by sealing outer portion 114 to inner portion 116 over at least part of the axial length thereof (not shown) to impede such rolling tendency.

Figure 14:
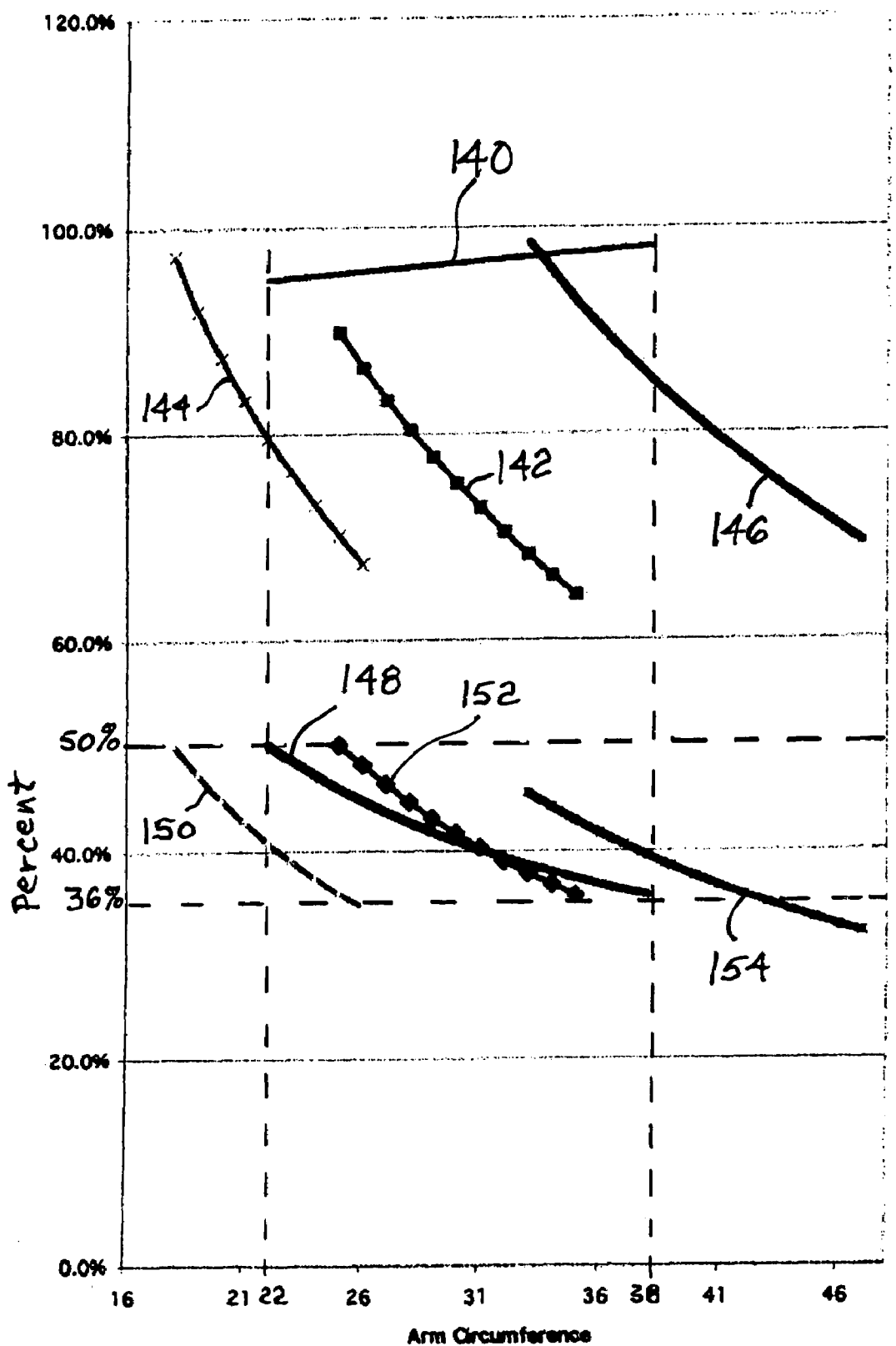
FIG. 14 is a graph showing comparing performance of a set of three prior art cuffs and an improved non-stiffened cuff in accordance with the invention.

The increased range of arm circumference over which the improved cuff is useful in shown in FIG. 14, wherein embodiment 113 is compared against a well-known prior art three-cuff closed cuff system, the Baumanometer, available from W.A. Baum Co., Inc., Copiague, N.Y., USA. The curves in the upper part of the graph deal with the percent arm circumference covered by the device, and the curves in the lower part of the graph deal with bladder width as a percentage of arm circumference.

Referring first to the upper curves, curve 140 shows that embodiment 113 encircles at least 95% of an arm from a circumference of as little as 22 cm (child) to as large as 38 cm (large adult). Recall that good medical practice requires that a cuff encircle at least 70% of the arm; thus, curves 142, 144, and 146 show the compromises usually made on existing wrap cuffs frequently violate this practice, particularly on larger arms. Because the bladder width of the existing wrap cuffs is selected to be correct in the middle of the range, it varies from the recommended 40% of arm circumference when used on smaller or larger arms. In the case of the Baumanometer Adult cuff, the width varies from as low as 36% on the largest arm specified to 50% on the smallest arm specified. The specified range is from 25 cm to 35 cm in circumference. Using the same width variation, the bladder 113 has a range of 22 cm to 38 cm in circumference, an increase of 60% in the range. Alternatively, if bladder 113 was specified to be used over the same range as the Baumanometer Adult cuff, the bladder width would remain considerably closer to the 40% goal. Further, because the improved cuff covers a range of arm sizes from 22 mm to 38 mm within the recommended range of bladder contact widths, almost all of the need for the small adult cuff and much of the need for the large adult cuff are eliminated.

Figure 15:
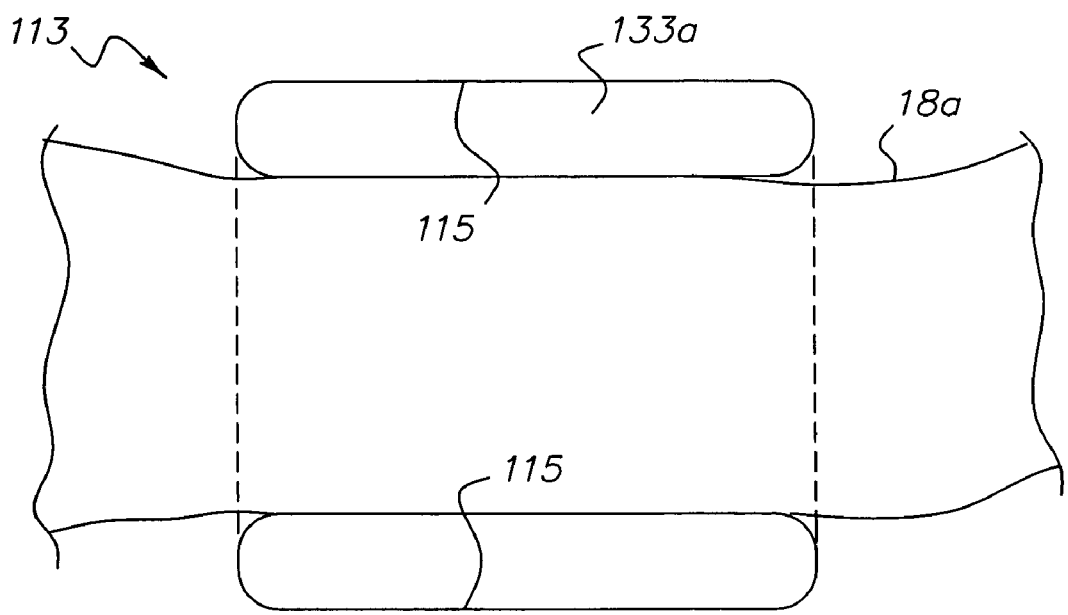
FIG. 15 is a schematic axial cross-sectional view of a non-stiffened cuff in accordance with the invention in use on a large-diameter arm.
Figure 16:
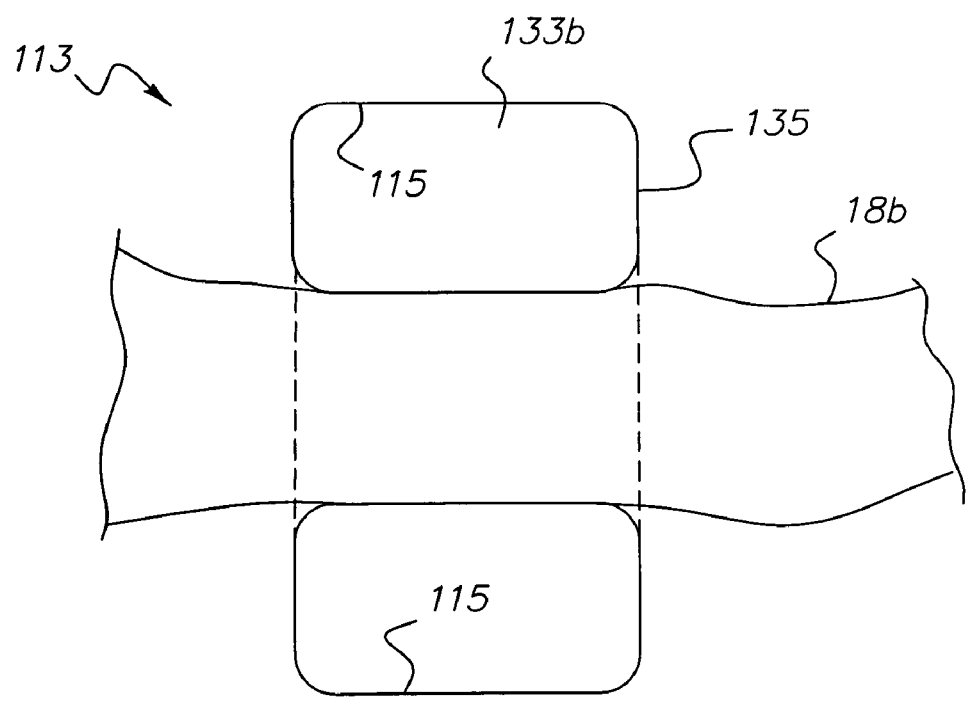
FIG. 16 is a schematic axial cross-sectional view of a non-stiffened cuff in accordance with the invention in use on a small-diameter arm.

FIGS. 15 and 16 show first embodiment 113 in two different degrees of inflation, corresponding to use in two different sizes of arms 18a,18b. For an arm 18a having a relatively large diameter and circumference (FIG. 15), bladder 113 assumes a surprisingly boxy cross-sectional shape 133a, having a relatively long cuff-width extent which is desirable for a large-diameter arm. For arms 18b having progressively smaller diameters and circumferences, bladder 113 assumes a still-boxy oval 133b having relatively straight sides 135 and having a progressively shorter cuff-width extent.

Figure 11:
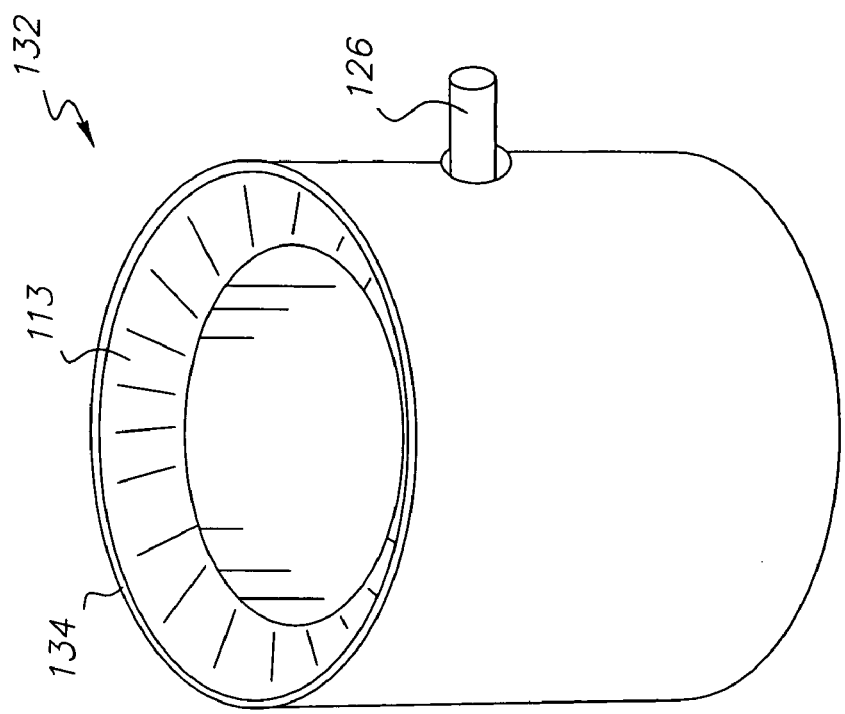
FIG. 11 is an isometric view of the second embodiment shown in FIG. 10, showing the bladder in a deflated position for placement onto an arm.
Figure 10:
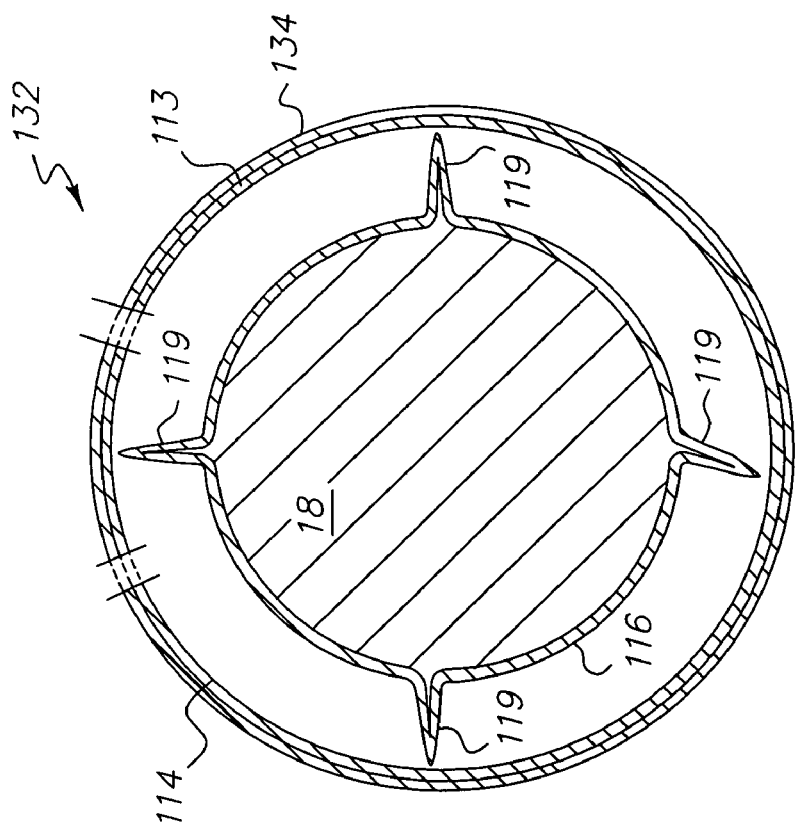
FIG. 10 is a transverse cross-sectional view of a second embodiment of an improved closed cuff in accordance with the invention, showing a continuous stiffener attached to the outside of the tubing element.

Referring to FIGS. 10 and 11, in a second embodiment 132 of a closed cuff in accordance with the invention, bladder 113 is reinforced by a continuous stiffener 134 that surrounds bladder 113 and may be attached to the inner or outer surface of outer portion 114 over at least a partial axial deflated length thereof. In a currently preferred embodiment, stiffener 134 is attached to the inside of the outer portion of bladder 113 and extends along less than the full deflated axial dimension thereof. Stiffener 134 also acts to prevent axial rolling of toroidal bladder 113 and in combination with bladder outer portion 114 defines a substantially cylindrical structure from which inner portion 116 may be freely inflated, both axially and radially of the toroid and inflated inwards.

Figure 13:
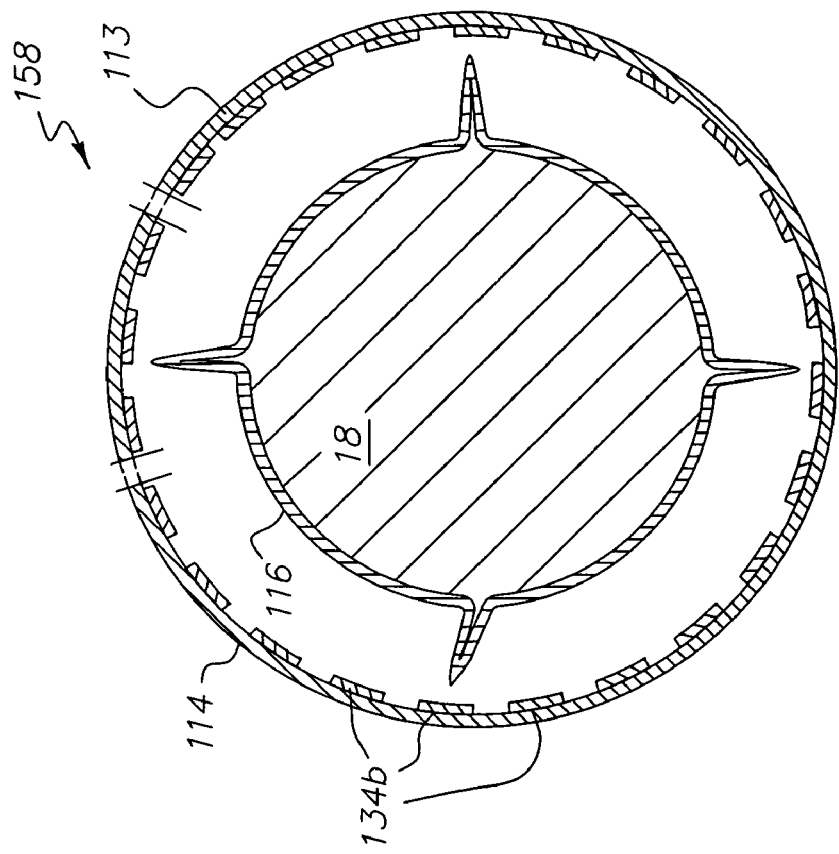
FIG. 13 is a transverse cross-sectional view of a fourth embodiment of an improved closed cuff in accordance with the invention, showing stiffener ribs attached to the inside of the bladder.
Figure 12:
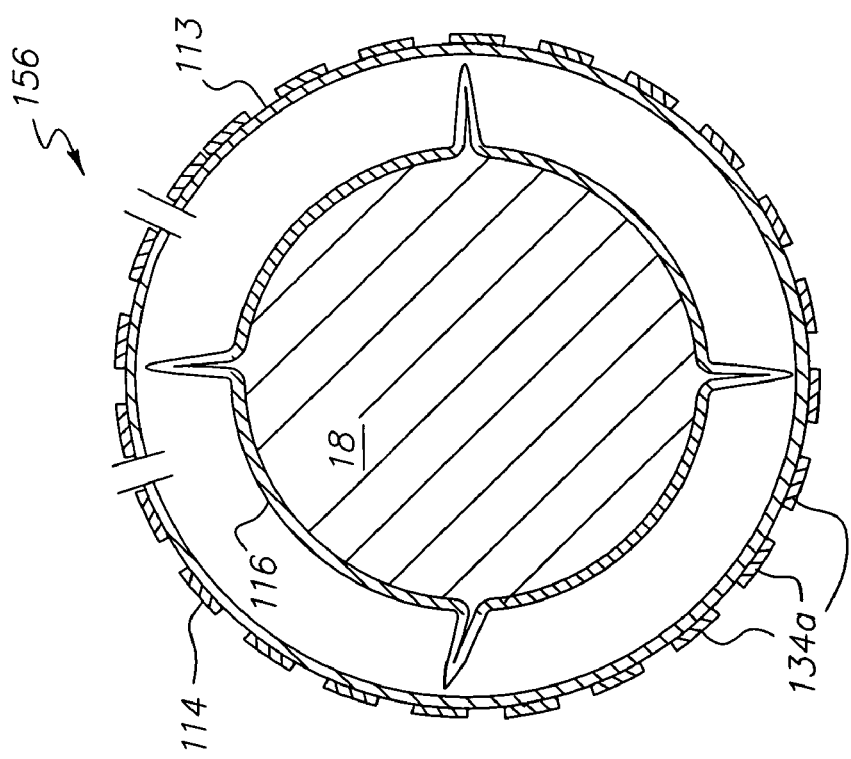
FIG. 12 is a transverse cross-sectional view of a third embodiment of an improved closed cuff in accordance with the invention, showing stiffener ribs attached to the outside of the bladder.

Referring to FIGS. 12 and 13, in third embodiment (156) and a fourth embodiment (158), respectively, a stiffener may be provided as a plurality of spaced-apart, axially-extending stiff ribs attached to the outer surface (embodiment 156, ribs 134a) or to the inner surface (embodiment 158, ribs 134b) of outer portion 114 of bladder 113. Such ribs provide the benefit of stiffener 134 in influencing favorably the shape of the bladder as it is inflated to a range of arm sizes. The ribs also permit the improved cuff to be folded flat for storage.

Figure 17:
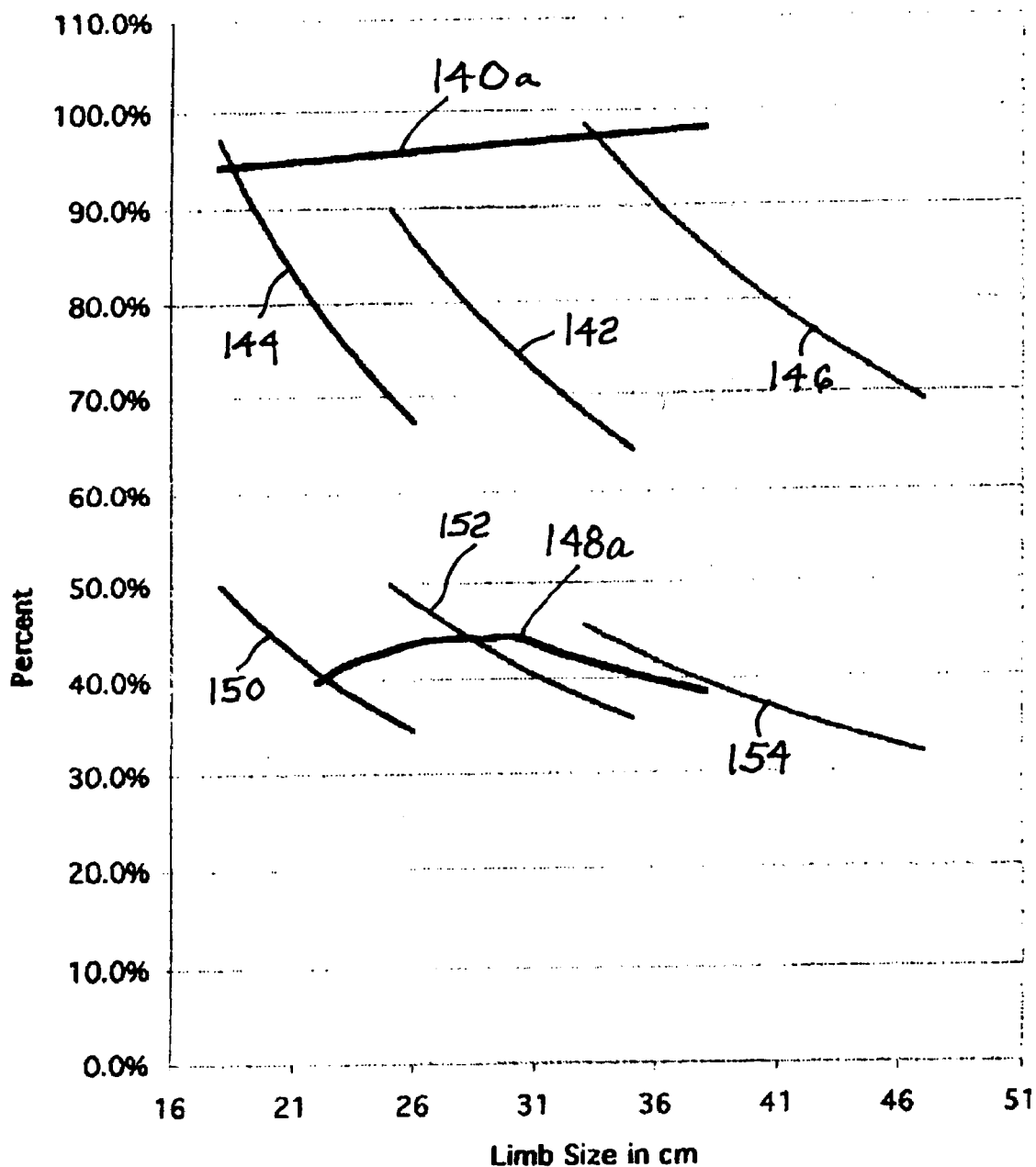
FIG. 17 is a graph like that shown in FIG. 14 but using an improved cuff stiffened in accordance with the invention.

Referring now to FIG. 17, the attachment of stiffener 134 improves still further the axial cross-sectional shape and performance of bladder 113 when used with different sizes of arm 18, in comparison with prior art cuffs. Prior art performance curves 142,144,146,150,152,154 are as already shown in FIG. 14. As before, a cuff in accordance with the invention provides greater than 90% circumferential limb coverage at all limb sizes (curve 140a). However, recall that the desired cuff contact width is about 40% of the cuff contact length. As FIG. 17 shows, the addition of stiffener 134 to bladder 113 improves the shape of the bladder at smaller limb sizes such that the range of contact lengths is always near the optimum 40% (curve 148a).

Figure 18:
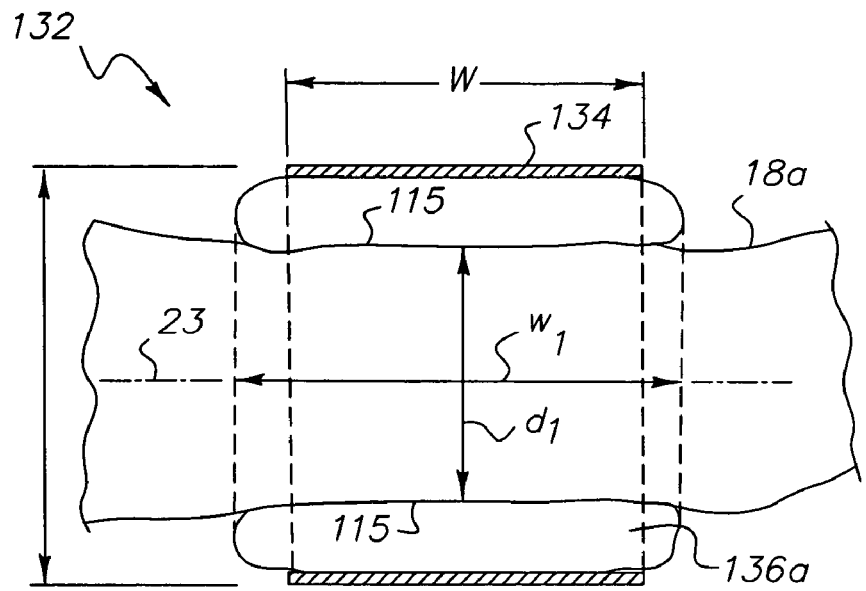
FIGS. 18-19 are views like those shown in FIGS. 15-16 but using a stiffened cuff.
Figure 19:
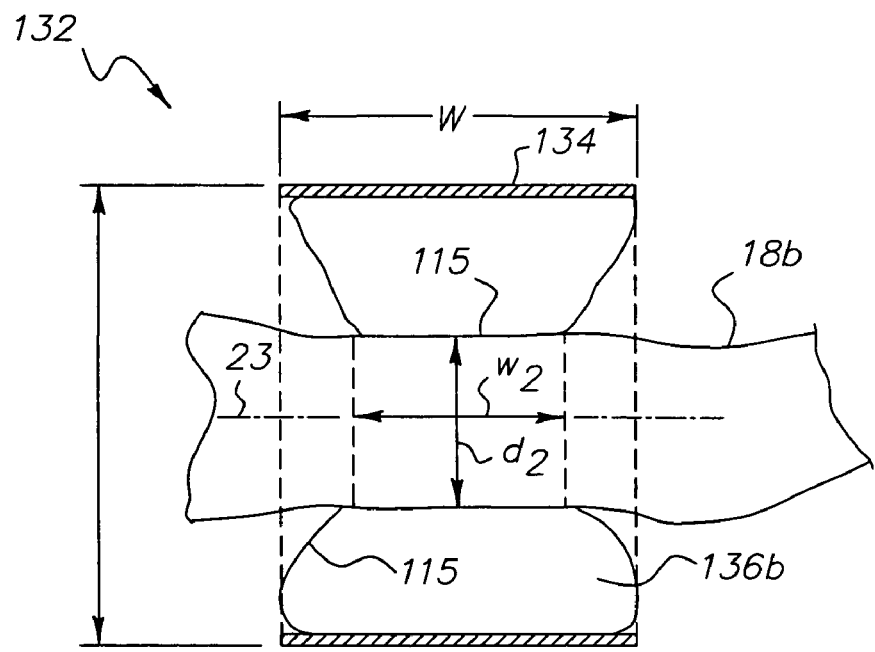

This improvement is shown in FIGS. 18 and 19, showing second embodiment 132 in two different degrees of inflation, corresponding to use in two different sizes of arms 18a,18b. Because the material of bladder 113 is non-distensible, the circumference 115 of the axial cross-section of the bladder itself is constant under all conditions of use. For an arm 18a having a relatively large diameter and circumference (FIG. 15), bladder 113 assumes a relatively flat oval 136a in cross-sectional shape (compare to shape 133a in FIG. 15), having a relatively long cuff-width extent which is desirable for a large-diameter arm.

For arms 18b having progressively smaller diameters and circumferences, bladder 113 assumes a trapezoidal shape 136b having a progressively shorter cuff-width extent (compare to the boxy shape 133b in FIG. 16). When embodiment 132 is sized for that relationship for the largest circumference (diameter may be used interchangeably for circumference in this discussion, since the relationship is fixed geometrically), the attachment of stiffener 134 allows the bladder to automatically assume a shorter cuff contact width as the arm diameter decreases, thus maintaining the desired relationship over a much wider range of arm sizes than is possible with a prior art cuff having all edges of the pneumatic chamber constrained (FIG. 2).

While this is a great advantage on automated machines, it is perhaps even more important in clinical practice. As a result of incorrect blood pressure measurements, individuals may be medicated for high blood pressure who really do not have elevated blood pressure. Because an improved cuff in accordance with the invention also is usable on larger arms, perhaps half of the wrong-size incorrect readings can be eliminated, especially those readings wherein a too-small prior art cuff is used on a too-large arm. Some studies estimate that wrong-size cuffs are used in 30% of the measurements in clinical practice, usually because a too-small cuff was used.

Further, an improved cuff does not have to be adjusted for each use as does a wrap-around cuff, nor does it require expertise to install. An improved cuff cannot be installed incorrectly, other than using it on an arm that is simply too small.

Referring still to FIGS. 18 and 19, the width W of stiffener 134 remains constant, but the cuff contact width w of bladder 42 decreases as the diameter d of the subject arm decreases. In this comparison, $w_1/d_1$ for arm 18a is about the same as $w_2/d_2$ for arm 18b. Thus, blood pressure measurements on the two arms are comparable for accuracy.

Figure 20:
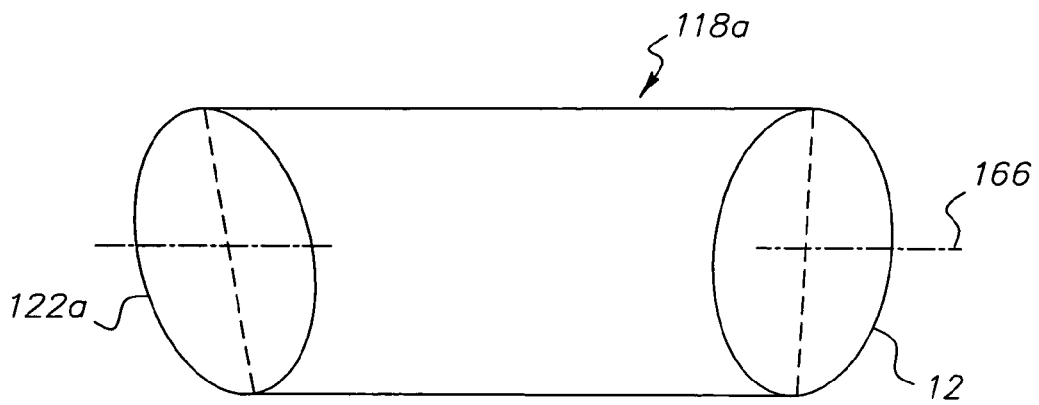
FIG. 20 is an isometric view showing a length of seamless tubing like the tubing shown in FIG. 5 but cut on the bias such that, when formed into a closed cuff by joining the ends, an axially tapered (frusto-conical) cuff may be formed.
Figure 21:
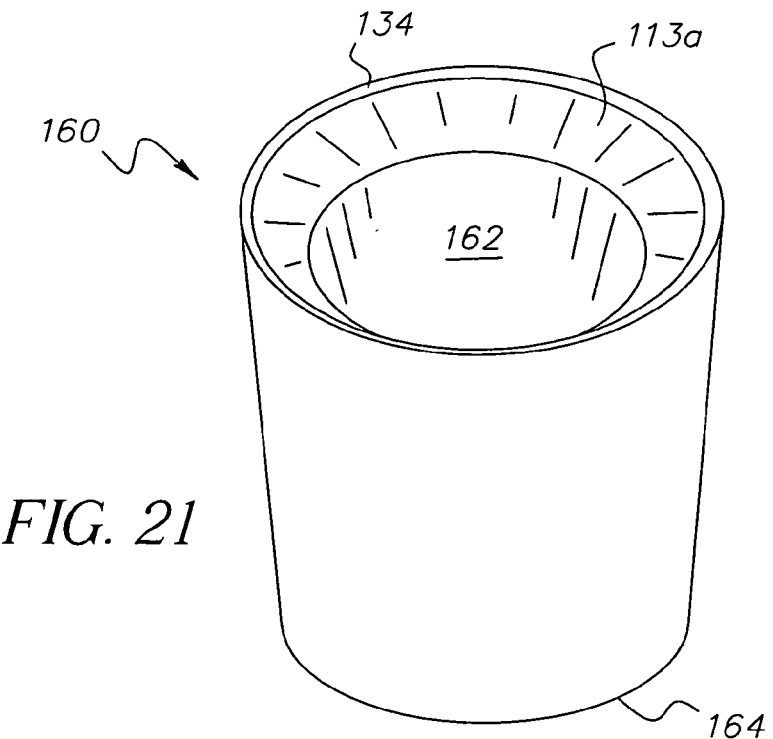
FIG. 21 is an isometric view of a frusto-conical cuff formed from the tubing shown in FIG. 20.
Figure 22:
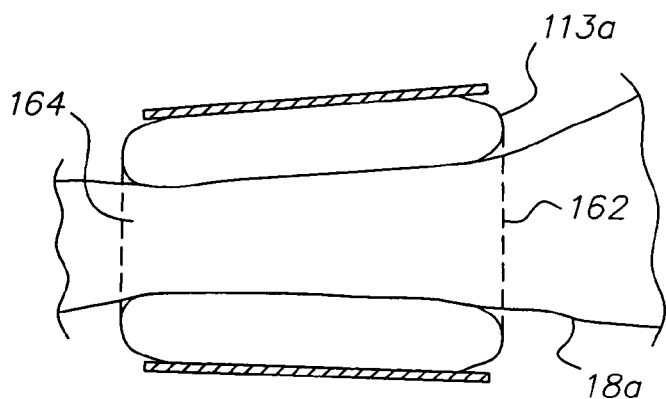
FIG. 22 is a schematic cross-sectional view like that shown in FIG. 18 but employing the tapered cuff shown in FIG. 21.

It is known that most actual arms exhibit a tapered shape, the arm circumference being greater near the shoulder than at the bicep, and both regions are larger than at the elbow. A flat cuff is easily misapplied on an arm that exhibits considerable taper because it has to be applied such that the cuff appears crooked. Very few arms lack this taper, except for very small arms such as children's arms. If the cuff is made in the form of a cylinder, it will not fit on some large arms because it is too small at the end near the shoulder. Referring to FIGS. 20 through 22, a tapered closed cuff 160 in accordance with the invention may be formed as a fructo-conical bladder having a large opening 162 and a small opening 164. Cuff 160 may be readily formed form a length of tubing 118a that has its ends 122a,124a cut on a bias to axis 166 such that joining of those ends as shown in any of FIGS. 4 and 7 through 9 yields a tapered bladder 113a. Preferably, bladder 113a is stiffened by addition of any of stiffeners 134,134a,134b as described above. As shown in FIG. 19, cuff 160 can readily conform to a large tapered arm 18a.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A closed cuff for use in inferential measurement of animal arterial blood pressures, comprising:
   an inflatable ring-shaped bladder having an inner portion and an outer portion,
   wherein said inner and outer portions are formed from non-distensible material,
   wherein said bladder is defined by a single tubular starting element formed into said ring shape by connecting opposite ends of said tubular starting element, defining a ring having a non-adjustable fixed outer circumference,
   wherein said outer portion remains outward of said ring and said inner portion remains inward of said ring such that the interior of said single tubular starting element defines a chamber for air inflation in blood pressure measurement,
   wherein said inner portion of said bladder is adapted to be in direct contact with a user's extremity when said cuff is in use, and
   wherein said bladder is unconstrained axially of said ring shape during inflation thereof and becomes toroidal in shape, and
   wherein said single tubular starting element is seamless.

2. A closed cuff for use in inferential measurement of animal arterial blood pressures, comprising:
   an inflatable ring-shaped bladder having an inner portion and an outer portion,
   wherein said inner and outer portions are formed from non-distensible material,
   wherein said bladder is defined by a single tubular starting element formed into said ring shape by connecting opposite ends of said tubular starting element, defining a ring having a non-adjustable fixed outer circumference,
   wherein said outer portion remains outward of said ring and said inner portion remains inward of said ring such that the interior of said single tubular starting element defines a chamber for air inflation in blood pressure measurement,
   wherein said inner portion of said bladder is adapted to be in direct contact with a user's extremity when said cuff is in use, and
   wherein said bladder is unconstrained axially of said ring shape during inflation thereof and becomes toroidal in shape, and
   wherein said single tubular starting element is formed from sheet stock and includes a longitudinal seam contained within said outer portion and apart from the conjunctive areas of said outer portion with said inner portion.

3. A cuff in accordance with claim 1 wherein a stiffener is attached to said outer portion of said bladder.

4. A cuff in accordance with claim 3 wherein said stiffener is disposed outside of said bladder.

5. A cuff in accordance with claim 3 wherein said stiffener is disposed within said bladder.

6. A cuff in accordance with claim 3 wherein said stiffener includes a continuous element.

7. A cuff in accordance with claim 3 wherein said stiffener includes a plurality of stiff ribs.

8. A cuff in accordance with claim 1 wherein the form of said ring-shaped bladder is selected from the group consisting of cylindrical and frusto-conical.

9. A cuff in accordance with claim 1 further comprising means connected to said ring-shaped bladder for inflating and deflating said bladder.

10. A cuff in accordance with claim 1 wherein said bladder is formed from material including polyurethane-coated nylon mesh.

11. A cuff in accordance with claim 1 wherein said cuff is suitable for use as a replacement cuff in a prior art device selected from the group consisting of prior art automated public use measurement device having a fixed closed cuff, prior art automated device allowing for a selection of cuffs by an operator, and prior art manual device allowing for a selection of cuffs by an operator.

12. A cuff in accordance with claim 1 wherein opposite ends of said single tubular starting element are joined to form a seam directed axially of said ring shape, wherein said toroidal shape and said chamber for air inflation are discontinuous, being interrupted by said seam.

13. A cuff in accordance with claim 1 wherein opposite ends of said single tubular starting element are joined to form a seam circumferential of said tubular starting element, wherein said toroidal shape and said chamber for air inflation are continuous, being non-interrupted by said circumferential seam.

14. A method for forming a ring-shaped closed cuff for measuring blood pressure, comprising the steps of:
   a) forming a single tubular starting element of non-distensible material, said single tubular starting element having first and second opposite ends and defining an interior space between said first and second opposite ends; and
   b) joining said first and second opposite ends to form said ring-shaped cuff wherein said interior space defines a chamber for inflation during said blood pressure measuring
   wherein said joining step includes the step of forming a seam directed axially of said ring shape, wherein said chamber for inflation is discontinuous, being interrupted by said seam.

15. A method for forming a ring-shaped closed cuff for measuring blood pressure, comprising the steps of:
   a) forming a single tubular starting element of non-distensible material, said single tubular starting element having first and second opposite ends and defining an interior space between said first and second opposite ends; and
   b) joining said first and second opposite ends to form said ring-shaped cuff wherein said interior space defines a chamber for inflation during said blood pressure measuring
   wherein said joining step includes the step of forming a seam circumferential of said tubular starting element, wherein said chamber for inflation is continuous, being non-interrupted by said circumferential seam.

16. An automated blood pressure measurement machine, comprising:
   a) a housing;
   b) an inflatable closed cuff disposed in said housing and including a ring-shaped bladder having an inner portion and an outer portion,
   wherein said bladder is formed from an air-impermeable, non-distensible material, wherein said bladder is defined by a single tubular starting element formed into said ring shape by connecting opposite ends of said tubular starting element to define a ring having a non-adjustable fixed outer circumference such that the interior of said single tubular starting element defines a chamber for air inflation, wherein said single tubular starting element is seamless, wherein said bladder is adapted to be in direct contact with a user's extremity when said cuff is in use, and wherein said bladder is unconstrained axially of said ring shape during inflation thereof and becomes toroidal in shape;

c) means for inflating said inflatable closed cuff; and d) means tor measuring pressure within said inflatable closed cuff.

17. An automated blood pressure measurement machine, comprising:

a) a housing;

b) an inflatable closed cuff disposed in said housing and including a ring-shaped bladder having an inner portion and an outer portion, wherein said bladder is formed from an air-impermeable, non-distensible material, wherein said bladder is defined by a single tubular starting element formed into said ring shape by connecting opposite ends of said tubular starting element to define a ring having a non-adjustable fixed outer circumference such that the interior of said single tubular starting element defines a chamber for air inflation, wherein said single tubular starting element is formed from sheet stock and includes a longitudinal seam contained within said outer portion and apart from the conjunctive areas of said outer portion with said inner portion, wherein said bladder is adapted to be in direct contact with a user's extremity when said cuff is in use, and wherein said bladder is unconstrained axially of said ring shape during inflation thereof and becomes toroidal in shape;

c) means for inflating said inflatable closed cuff; and d) means for measuring pressure within said inflatable closed cuff.

* * * * *